(12) United States Patent
Slemker

(10) Patent No.: US 6,979,355 B1
(45) Date of Patent: *Dec. 27, 2005

(54) VALVE ASSEMBLY FOR A PROSTHETIC LIMB

(75) Inventor: Tracy C. Slemker, Clayton, OH (US)

(73) Assignee: The Ohio Willow Wood Company, Mount Sterling, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/947,668

(22) Filed: Oct. 9, 1997

Related U.S. Application Data

(63) Continuation of application No. 08/516,557, filed on Aug. 18, 1995, now Pat. No. 5,702,489.

(51) Int. Cl.$^7$ ................................. A61F 2/80
(52) U.S. Cl. .................................. 623/34; 623/36
(58) Field of Search ..................... 623/27, 32, 33, 623/34, 35, 36, 37, 57

(56) References Cited

U.S. PATENT DOCUMENTS

| | | | |
|---|---|---|---|
| 708,685 A | | 9/1902 | White ........................ 623/37 |
| 980,457 A | * | 1/1911 | Toles ......................... 623/36 |
| 1,996,377 A | | 4/1935 | Hinchen ..................... 223/111 |
| 2,464,443 A | | 3/1949 | Ganoe ........................ 623/36 |
| 2,530,285 A | * | 11/1950 | Catranis ..................... 623/44 |
| 2,569,790 A | | 10/1951 | White et al. | 
| 2,790,180 A | * | 4/1957 | Hauser ....................... 623/36 |
| 3,377,416 A | * | 4/1968 | Kandel ....................... 623/34 |
| 3,712,298 A | * | 1/1973 | Snowdon .................... 128/40 |
| 4,128,903 A | | 12/1978 | Marsh et al. | 
| 4,655,779 A | | 4/1987 | Janowiak .................... 623/37 |
| 5,007,937 A | | 4/1991 | Fishman et al. | 
| 5,133,776 A | * | 7/1992 | Crowder ..................... 623/37 |
| 5,139,523 A | * | 8/1992 | Paton ......................... 623/37 |
| 5,163,965 A | * | 11/1992 | Rasmusson ................. 623/36 |
| 5,376,127 A | | 12/1994 | Swanson | 
| 5,376,131 A | | 12/1994 | Lenze et al. | 
| 5,549,709 A | | 8/1996 | Caspers ...................... 623/24 |
| 5,658,353 A | * | 8/1997 | Layton ....................... 623/34 |
| 5,904,722 A | * | 5/1999 | Caspers ...................... 623/34 |
| 5,980,577 A | * | 11/1999 | Radis ......................... 623/36 |
| 6,021,935 A | * | 2/2000 | Yonezawa ................... 223/111 |
| 6,287,345 B1 | * | 9/2001 | Slemker et al. ............. 623/34 |

FOREIGN PATENT DOCUMENTS

| | | | | |
|---|---|---|---|---|
| DE | 27 29 800 | * | 1/1979 | ............ A61F 1/02 |
| EP | 0019612 | | 5/1980 | |
| EP | 0363654 | | 4/1990 | |
| JP | 07155343 | * | 6/1995 | .................. 623/34 |
| RU | 311633 | | 4/1970 | |
| RU | 1598999 | | 7/1988 | |
| SE | 8801686 A | * | 3/1989 | ............ A61F 2/78 |

OTHER PUBLICATIONS

English tranlation of Plotnik, SU 305888.*

* cited by examiner

*Primary Examiner*—David H. Willse
(74) *Attorney, Agent, or Firm*—Standley Law Group LLP

(57) ABSTRACT

A prosthetic limb comprises a socket for receiving a patient's residual limb, and an upright assembly. The socket includes a base provided in its distal end. The base includes a chamber therewithin and an channel for providing fluid communication between the chamber and the interior of the socket. A duct extends through the socket and engages the base such that it is in fluid communication with the chamber. A valve is coupled to the duct to allow controlled or forced gas transfer to and from the interior of the socket. A seal is provided between the base and the socket to facilitate suction between the patient's residual limb and the socket.

19 Claims, 2 Drawing Sheets

VALVE ASSEMBLY FOR A PROSTHETIC LIMB

This is a continuation of application Ser. No. 08/516,557 filed Aug. 18, 1995.

BACKGROUND

The present invention relates generally to prosthetic devices and, more particularly, to a valve assembly for use with a prosthetic limb socket.

A prosthesis is often used to replace an amputated portion of a limb and to help restore the amputee's ability to use that limb. A prosthesis for a lower extremity amputation will often include an artificial foot connected to an upright assembly (pylon, tube or shaft) which is in turn connected to a custom fitted socket assembly (it is also known in the art to use non-custom fitted socket assemblies). If the amputation is an above-the-knee amputation, the upright assembly will commonly include an artificial knee joint.

An above-the-knee prosthesis typically requires two interlaying sockets; an inner socket consisting of a flexible, thermoplastic material, and a stronger, less flexible, thermoplastic outer socket which is attached to the upright-assembly of the prosthesis. The inner socket is typically designed to interface with and cushion the amputee's residual limb, to protect the amputee's residual limb from the interconnection components which attach the socket assembly to the upright assembly, and to provide an air-tight seal between the residual limb and the outer socket.

This type of prosthesis is typically held on the patient by suction formed in the socket. Therefore, the inner socket will typically include a valve system positioned in the distal inner thigh portion of the socket assembly to release air trapped between the wearer's residual limb and the inner socket as the wearer is inserting the residual limb into the socket. After insertion of the residual limb in the socket, the valve system will be closed, thus forming the suction within the socket.

One typical valve system includes an annular valve housing permanently formed into a projection extending from the inner socket, and a valve which is usually threadedly engaged within a threaded hole in the annular valve housing. Such a valve system is typically constructed such that it protrudes from the inner socket through a hole in the outer socket to provide access to the valve system. Construction of the inner socket for this type of valve system typically includes the step of drape forming or blister forming a thermoplastic socket cone over a socket mold having the valve housing attached thereon. The valve housing will thus be vacuum formed or permanently laminated into the socket during fabrication of the socket. Excess plastic is then ground from around the valve housing to expose and facilitate access to the threaded hole in which the valve will engage. A valve can then be threadedly engaged into the valve housing such that gas may be transferred through the valve.

A disadvantage with such a fabricating process is that during the blister forming operation the plastic cone will catch on the fabrication plate and will periodically stretch thin in that area. Also, the transition from the inner surface of the socket to the valve can be very rough and uneven. Furthermore, because the valve housing is permanently molded into the socket, if there is a failure in the valve housing the entire inner socket may need to be re-fabricated.

Another typical valve system includes a valve housing comprised of two pieces. An annular housing member extending through the inner socket, having an annular flange for providing a seat and a seal against the inner surface of the socket; and an annular nut member which threadedly engages the outer circumference of the annular housing member extending from the inner socket. Once the nut member is threaded on the housing member, thus attaching the housing to the socket, a valve can then be threadedly engaged within the valve housing. Construction of the inner socket for this type of valve system will typically include the step of vacuum forming a thermoplastic preform cone over a positive cast of the amputee's residual limb having a definition-plate attached to the positive cast in the location of the vacuum housing. Once the socket is formed, a hole will be drilled into socket projection formed by the definition plate to facilitate insertion of the valve housing member.

A disadvantage with this type of valve system is that the thickness of the socket around the valve housing is unpredictable, and therefore, the fit of the valve housing within the socket will also be unpredictable.

An additional disadvantage with both valve systems described above is that, because of the inner thigh location of the valves, when the residual limb is inserted into the sockets the valve systems do not release air directly from the distal end (or bottom) of the sockets. The distal end of the limb may cover and seal off the valves in the sockets before the limb can be completely inserted into the sockets, preventing air from being released from the sockets. This may result in an undesirable air pocket between the distal limb and the distal end of the sockets.

Another disadvantage with the above valve systems is the requirement of the two sockets. Besides the added time and expense of creating an inner socket in the first place, if the inner socket needs to be re-fabricated due to damage or needs to be re-fitted due to a change in the limb dimensions, the hole on the outer socket for the valve may no longer align with the valve projection protruding from the inner socket. Furthermore, two sockets can give the prosthesis a long profile; thus if the amputation is immediately above the knee, the prosthesis may undesirably extend the thigh portion beyond where the knee joint should be.

Yet another disadvantage with the above valve systems is that the valve systems do not facilitate the forced suction of gas from, or the forced injection of gas into the socket. Oftentimes the volumetric dimensions of the residual limb will change within a very short period of time due to fluid retention or fluid loss. A volumetric loss can result in socket retention problems, which could be corrected using forced suction. A volumetric gain can result in the residual limb being mechanically locked into the socket; and removal of the socket in such an instance could be greatly assisted using forced air injection.

Accordingly, a need exists for an improved valve system which will reduce the amount of skill, time, and equipment needed to fabricate or replace a prosthesis. A need exists for a valve system which helps to reduce the levels of variance in the socket fabrication processes. A need exists for a valve system which facilitates easier donning of the prosthesis by reducing time and effort required by the amputee to attach the prosthetic limb to the residual limb. Furthermore, a need exist for a valve system which facilitates forced suction and forced injection of air from and into the socket.

SUMMARY OF THE INVENTION

The present invention is a valve assembly for a prosthetic limb which responds to the problems associated with the prior prosthetic limb devices and valve systems. More particularly the present invention provides a cylindrical or hemispherical valve plate for insertion into the distal end of a prosthetic limb socket. In a preferred embodiment the present invention is used with the interface connector disclosed in U.S. Pat. No. 5,662,715, entitled "MODULAR INTERFACE CONNECTOR FOR A PROSTHETIC LIMB") by T. C. Slemker, the disclosure of which is hereby incorporated by reference.

In accordance with the present invention, the valve assembly includes a base which is fitted within the distal end of the socket. The base includes a chamber therewithin and an channel extending through the proximate surface of the base for providing fluid communication between the chamber and the interior of the socket. The valve assembly also includes a duct extending through the socket engaged with the base, which is in fluid communication with the chamber. A valve is coupled to the duct outside of the socket and an air tight seal is provided between the base and the socket so that a suction fit can be achieved as described below.

In a preferred embodiment an interface cushion member is mounted in the distal end of the socket and engaged with the base. The cushion includes a cavity which opens on its distal end and a projection extending radially around the mouth the cavity such that the base is retained in the cavity by the projection. The cushion member also includes at least one channel extending therethrough which provides fluid communication between the cushion member cavity and the interior of the socket. The projection of the cushion member includes a passage through which the duct extends and also provides the air tight seal between the base and the socket.

In the above preferred embodiment the base further includes a means for releasably attaching the base within the socket and means for releasably attaching the prosthetic limb upright assembly to the distal end of the socket. The cushion member preferably includes a substantially concave proximate surface which has a flexible feathered periphery extending radially outward from the surface, such that the interface cushion is adapted to abut the amputee's residual limb and such that the transition from the inner surface of the socket to the approximate surface of the interface cushion is substantially smooth without wrinkles or creases.

In operation, as the amputee's residual limb is inserted into the socket, the excess air escapes from within the socket through the valve assembly in the distal end of the socket. Once the residual limb is inserted comfortably within the socket the valve is closed, forming a suction such that the socket will be secured to the amputee's residual limb.

Alternatively, a quick-disconnect port on the valve could be utilized to force suction from, or inject gas into, the socket. Therefore, the forced transfer of air could correspondingly assist in the donning and removal of the prosthesis to and from the patients residual limb.

DETAILED DESCRIPTION

Figure 1:
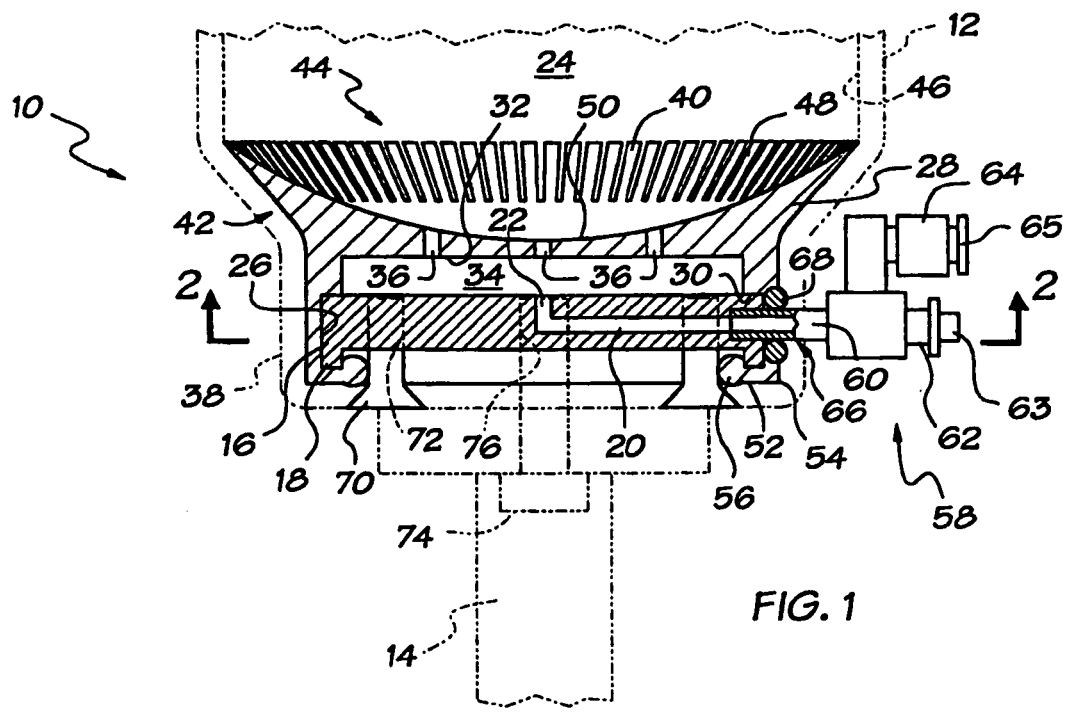
FIG. 1 is a cross sectional view of the valve assembly of the present invention.
Figure 2:
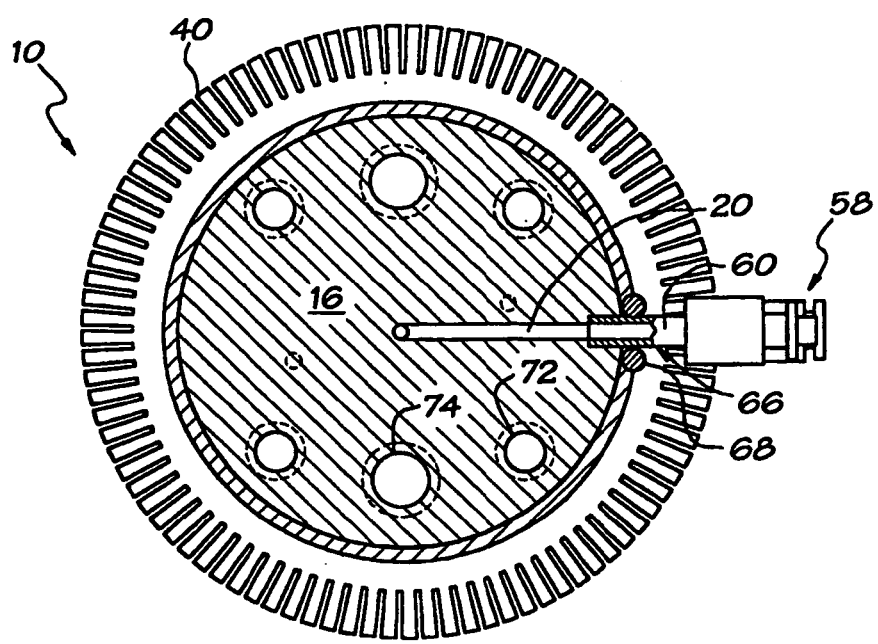
FIG. 2 is a cross sectional view taken along lines 2—2 of FIG. 1.
Figure 3:
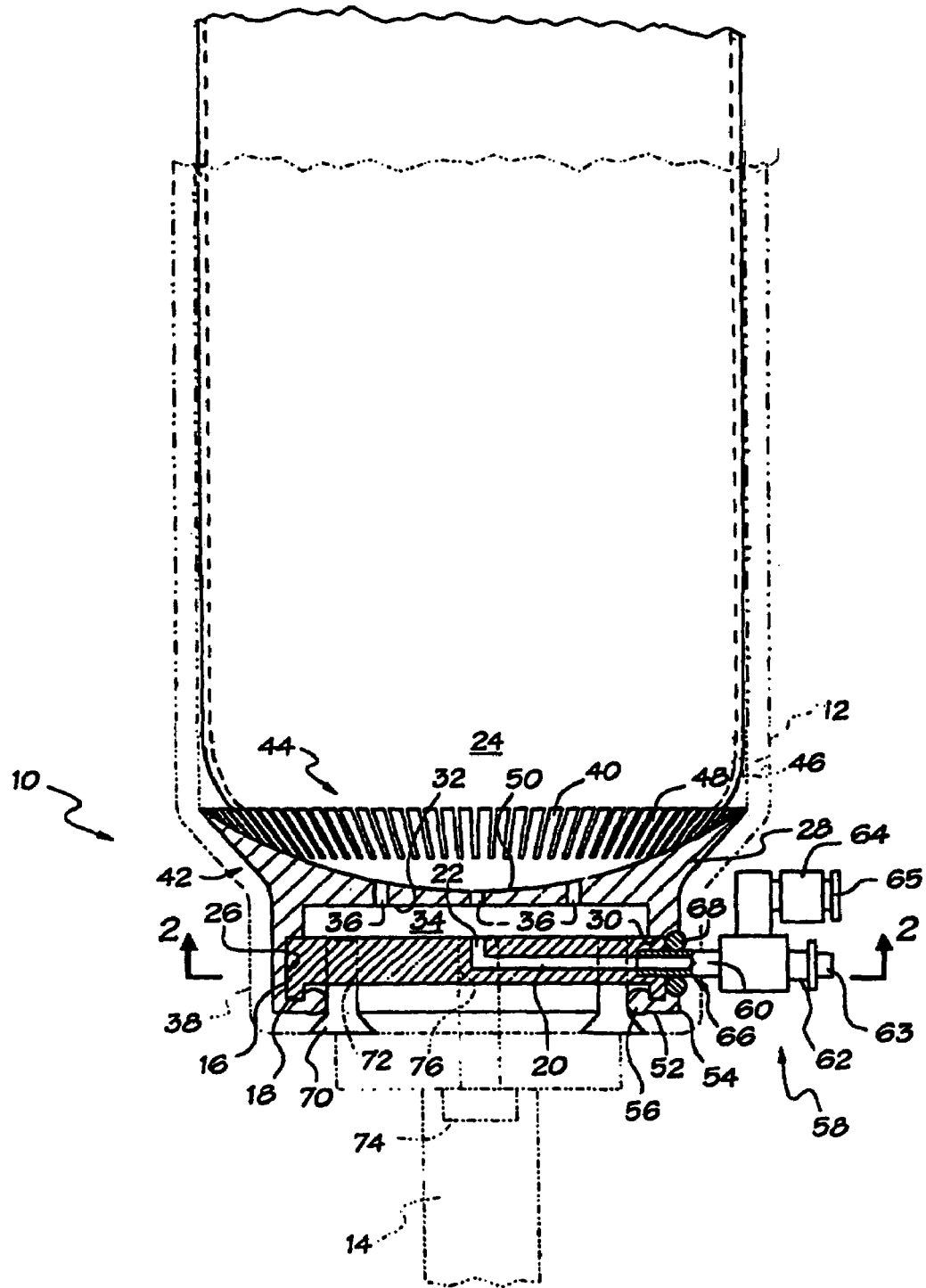
FIG. 3 illustrates a liner-covered residual limb inserted into the prosthetic limb socket of FIG. 1.

As shown in FIG. 1 the valve assembly of the present invention, generally depicted as 10, is used to facilitate the donning and removal of the prosthetic limb on a patient's residual limb. In a preferred embodiment, the valve assembly is also used as a interface connector for connecting an upright assembly 14 to a distal end of a prosthetic limb socket 12.

The preferred embodiment of the valve assembly 10 includes a cylindrically shaped stainless-steel base plate 16 having an annular rim 18 extending distally from the periphery of the base plate 16. The base plate 16 includes an inner chamber 20 existing therewithin and an channel 22 which provides fluid communication between the socket interior 24 and the inner chamber 20.

It is noted that although the base is preferably substantially cylindrically shaped, other shapes adapted to fit the base within a distal end of the socket will suffice. For example, it is within the scope of the invention that the base be substantially hemispherically shaped, such as to fit the base within a cup-shaped distal end of a socket. Similarly, the base can be constructed of any rigid, non-permeable material or materials in place of the preferred stainless-steel material.

In the preferred embodiment, an interface cushion 28 is mounted over the base plate 16 by inserting the base plate 16 within a cylindrical cavity 26 existing in a distal end of the interface cushion 28. The cavity 26 has an annular shoulder 30 which prevents the base plate 16 from abutting a proximate surface 32 of the cavity 26 such that the base plate 16 is retained in the cavity 26 to form an intermediate air chamber 34 between the base plate and the interface cushion. The interface cushion 28 includes a plurality of channels 36 to provide fluid communication between the socket interior 24 and the intermediate air chamber 34. It also is within the scope of the invention to fill the intermediate air chamber 34 with a removable porous pad (not shown), to provide additional cushioning.

The interface cushion 28 is shaped to fit within a distal socket extension 38 of the socket 12; however, it also is within the scope of the invention that the interface cushion be adapted to fit within a distal end of a socket not having a socket extension. The interface cushion is preferably made from a thermoplastic polyurethane such as Santaprene (a registered trademark of Monsanto Corporation). It is also within the scope of the invention to construct the interface cushion from any flexible material capable of providing sealing capabilities required from the invention as described below.

In the preferred embodiment, the interface cushion 28 has a multitude of tapered blades 40 extending from the outer periphery of the proximate end 42 of the interface cushion, giving the interface cushion a flexible feathered periphery 44 which conforms to the inner surface 46 of the socket 12 when the interface cushion is inserted into the socket extension 38. The proximate surfaces 48 of the blades are flush with a concave proximate surface 50 of the interface cushion. The feathered periphery 44 allows the concave proximate surface 50 of the interface cushion to smoothly transition into the inner surface 46 of the socket, substantially without the formation of creases or wrinkles.

An annular shoulder 52 extends radially inward from an outer rim 54 of the cavity 26, and projects over the annular rim 18 of the base plate 16 to retain the base plate 16 within the cavity 26. An annular o-ring projection 56 extends radially inward from the shoulder 52 and engages the rim 18 to form an air-tight seal between the base plate 16 and the socket 12.

A valve 58 having a valve duct 60 extends through the socket 12 and is engaged with the base plate 16 such that the duct 60 is in fluid communication with the base plate chamber 20. The valve duct 60 extends through a passage 66 in the interface cushion and an air-tight seal 68 is provided to seal the duct from the socket. Preferably, the valve has two ports, an open/close or needle-valve port 62 and a quick disconnect port 64. Such a flow control valve is commercially available from SMC Corporation, Tokyo, Japan, as a "Series AS" Direct Connection Type, Speed Controller With One-touch Fittings.

The open/close port 62 operates as follows: rotating or screwing a needle-valve handle 63 on the open/close port 62 clockwise closes the valve, and rotating the handle 63 counter-clockwise opens the valve. The quick-disconnect port 64 operates as follows: to attach a pump tube (not shown), a release bushing 65 is pulled out to an unlock position and the pump tube is inserted in the port 64. By releasing the bushing 65, the bushing returns to the locked position, and the pump tube becomes locked into the port. At this point, the pump is then able to either inject gas through the valve 58 into the socket, or to suck gas through the valve 58 from the socket. To remove the pump tube, the bushing 65 is again pulled out to the unlock position, which allows the pump tube to be taken from the port.

It is noted that although the valve 58 described above is preferred, it is within the scope of the invention to provide a valve having only one of the two types of ports, and it is also within the scope of the invention to alternatively utilize any valve mechanism which allows and/or forces the transfer of gases to and from the prosthetic limb socket. The valve 58, or one of the valve ports, could alternatively be the type of valve which allows the transfer of gas in only one direction. Such a valve is conventionally known as a leak-rate valve. This type of valve could be configured to allow gas to be released from the socket while simultaneously restricting gas from being sucked back into the socket. This would help to enhance the suction fit of the socket on the patients residual limb.

The valve plate assembly 10 is releasably attached in the socket extension 38 by four screws 70 extending through holes in the distal end of the socket and engaged by threaded holes 72 in the base plate 16. The upright assembly 14 is releasably attached to the distal end of the socket by two bolts 74 extending from the upright assembly, through holes in the distal end in the socket and engaged by threaded holes 76 in the cylindrical base plate 16. In the present embodiment, the bolts and screws must be sealed to avoid leakage through their respective holes, using a silicone seal or a commercially available product known as "242 Loctite."

It is within the scope of the invention that the bolts 74, or similar attachment means, can be used to attach the upright assembly 14 to the socket 12 and the base plate 16 within the socket 12, without the need for additional attachment means. The valve assembly 10 can also be either permanently or temporarily bonded into the socket by use of epoxy or hook and pile mechanisms, or any other known means for such an attachment. The preferred embodiment of the invention operates as follows. Before the patient inserts his or her residual limb into the socket, it is preferred that the patient roll a silicone sleeve over the residual limb. The silicone sleeve helps protect the limb and provides a seal between the limb and the socket when the limb is tightly fitted in the socket. It is noted here that even though a silicone sleeve is preferred, the present invention is especially designed to allow the patient to don a prosthetic limb without having to wear any external sleeve at all; although it is preferred that the patient at least apply some sort of lubrication to the residual limb facilitate in donning and removal of the prosthesis. With or without an added sleeve, the combination of the interface cushion and the valve plate will simultaneously lock the patient's residual limb in the socket and will suitably protect and comfort the limb in the socket.

Before inserting his or her limb into the socket, the patient will first set the valve port 62 to the open position. At this valve setting the residual limb can be easily inserted into the socket 12 and the excess air will be forced through the valve plate assembly 10 and out through the open valve port 62. Once the residual limb is inserted comfortably in the socket 12, against the concave surface 50 of the interface cushion 28, the patient then closes the valve port 62. Thus, because of the seals provided by the invention 56, 68, suction is formed which secures the patient's residual limb within the socket, and the distal position of the valve plate assembly guarantees that substantially no air pockets are left between the patient's residual limb and the interface cushion 28.

To remove the residual limb from the socket the valve port 62 is opened again thus breaking the seal and allowing air to be brought into the socket through the valve plate assembly such that the residual limb can be easily removed from the socket.

The quick-disconnect port 64 of the valve provides an alternate means for the patient to insert or remove his or her residual limb from the socket 12. A pump mechanism may be attached to this quick disconnect port so as to force suction from or to force gas injection through the valve. Such a mechanism can be as simple as a hand-held pump, or it can be an electronically or hydraulically controlled device. To facilitate donning of the prosthetic limb, the residual limb will be inserted into the socket and the hand-held air pump is inserted into the quick disconnect port. The pump is then operated to suck the air from the socket and simultaneously suck the patient's limb into the socket. When the patient wishes to remove the residual limb from the socket, the pump is again inserted into the quick disconnect port and the pump is operated to inject air into the socket thus forcing the patient's residual limb from the socket.

Having described the invention in detail and by reference to the drawings, it will be apparent that modifications and variations are possible without departing from the scope of the invention as defined in the following claims.

What is claimed is:

1. A prosthetic limb socket and valve assembly, comprising:
   a substantially impermeable sleeve to be worn over a residual limb, said sleeve having an inner surface and an outer surface;
   a base attached to an interior distal end of said socket, said base including at least one channel interior thereto for connecting an interior of said socket to an exterior of said socket, said base located within said socket such that said channel remains unblocked by said residual limb until said residual limb is fully inserted into said socket;
   an interface attached to a proximal surface of said base and having a proximal face positioned to receive a distal end of said residual limb upon its insertion into said socket, said interface provided with one or more passages therethrough for connecting said socket interior to said at least one channel;
   a duct extending through said socket and connected to said channel; and
   a valve coupled to said duct for controlling the flow of air through said channel caused by insertion of said residual limb into said socket;
   wherein the sleeve-covered residual limb is retained in said socket by means of a vacuum created by expelling air in said socket through said valve assembly, said vacuum maintained by sealing contact between said outer surface of said sleeve and interior walls of said socket; and wherein substantially no air pockets remain between said distal end of said residual limb and said proximal face of said interface once said residual limb has been fully inserted into said socket.

2. The prosthetic limb and valve assembly of claim 1, wherein said valve is coupled to a pump which provides a forced transfer of air to or from the socket interior.

3. The prosthetic limb and valve assembly of claim 1, wherein said base includes an attachment means adapted to releasably attach an upright assembly to the distal end of the socket.

4. The prosthetic limb and valve assembly of claim 1, wherein said base is adapted to be removably fitted within the socket interior at the distal end of the socket.

5. The prosthetic limb and valve assembly of claim 1, wherein said interface comprises a flexible cushion.

6. A prosthetic limb comprising:
a substantially impermeable sleeve to be worn over a residual limb;
a socket having a distal end, and an interior including a receiving cavity configured to substantially conform to the exterior of a wearer's sleeve-covered residual limb, said receiving cavity having an inner surface that provides sealing contact with a substantial portion of an outer surface of said sleeve; and
a valve assembly including a residual limb interface attached to a subjacent base that is removably installed at a distal end of said receiving cavity, said valve assembly providing a fluid pathway from said receiving cavity through said base, said valve assembly located such that fluid transfer from within said receiving cavity is enabled prior to full insertion of said residual limb into said socket;
wherein insertion of said residual limb into said socket forces air in said socket out through said valve assembly, thereby creating a vacuum within said receiving cavity that retains said residual limb and is maintained by said sealing contact between said inner surface of said receiving cavity and said outer surface of said sleeve; and
wherein substantially no air pockets remain between a distal end of said residual limb and a mating surface of said residual limb interface once said residual limb has been fully inserted into said socket.

7. The prosthetic limb of claim 6, wherein said valve is coupled to a pump which provides a forced transfer of air to or from the socket interior.

8. The prosthetic limb of claim 6, wherein said base includes a proximal surface having at least one channel extending therethrough.

9. The prosthetic limb of claim 8, wherein the shape of said base is adapted to mimic the shape of the socket interior at the distal end of the socket.

10. The prosthetic limb of claim 8, wherein said base includes an attachment means adapted to releasably attach an upright assembly to the distal end of the socket.

11. The prosthetic limb of claim 8, wherein said residual limb interface comprises a flexible cushion.

12. A prosthetic limb, comprising:
a prosthetic limb socket shaped for receiving a patient's residual limb, said socket having a socket wall forming a socket interior and a socket exterior, said socket having a proximal opening, and a distal end;
an external prosthetic limb assembly for attachment to said socket exterior at said distal end of said prosthetic limb socket;
a base fitted within said socket interior at said distal end of said socket, a periphery of said base providing an air-tight seal with said socket wall, said base further including a channel opening onto said socket interior;
an attachment mechanism, carried on said base, for facilitating releasable attachment of said prosthetic limb assembly to said exterior distal end of said prosthetic limb socket; and
a valve coupled to said base for controlling the flow of air through said channel.

13. The prosthetic limb of claim 12, wherein a substantially annular projection extending from said base is used to provide said air-tight seal between said base and said socket wall.

14. The prosthetic limb of claim 12, further comprising a sleeve for placement over said residual limb prior to insertion of said residual limb into said prosthetic limb socket.

15. A prosthetic limb, comprising:
a prosthetic limb socket shaped for receiving a patient's residual limb, said socket having a socket wall, a socket interior, a proximal opening, and a distal end;
an upright assembly;
a base-plate fitted within said socket interior at said distal end of said socket, said base-plate including a channel extending into said base-plate and opening onto said
a valve coupled to said base-plate for controlling the flow of air through said channel; and
a bolt extending from said upright assembly, through said socket wall and into said base-plate;
whereby said base-plate facilitates the passage of air from said socket interior and also facilitates the coupling of the upright assembly to an exterior distal end of said socket.

16. The prosthetic limb of claim 15, further comprising an air-tight seal between said base-plate and said socket wall.

17. The prosthetic limb of claim 15, further comprising a sleeve for placement over said residual limb prior to insertion of said residual limb into said prosthetic limb socket.

18. A prosthetic limb, comprising:
a prosthetic limb socket shaped for receiving a patient's residual limb, said socket having an open socket interior formed by walls and a bottom, a proximal opening, and a distal end;
a base-plate fitted within said socket interior at said bottom thereof, said base-plate having an interface attached to a proximal portion thereof and adapted to abut said residual limb once it is properly inserted into said socket, said base-plate further including a channel extending into said base-plate and opening onto said socket interior; and
a port communicating with said channel, said port facilitating the coupling of a pump thereto so as to provide a forced transfer of air to or from said open socket interior through said channel and said base-plate;
whereby said residual limb can be drawn into or forced out of said prosthetic limb socket by said forced transfer of air; and
wherein substantially no air pockets remain between a distal end of said residual limb and an abutting surface of said interface when said residual limb has been fully drawn into said socket.

19. The prosthetic limb of claim 18, further comprising a sleeve for placement over said residual limb prior to insertion of said residual limb into said prosthetic limb socket.

* * * * *

UNITED STATES PATENT AND TRADEMARK OFFICE
CERTIFICATE OF CORRECTION

PATENT NO. : 6,979,355 B1
DATED : December 27, 2005
INVENTOR(S) : Tracy C. Slemker It is certified that error appears in the above-identified patent and that said Letters Patent is hereby corrected as shown below:

Column 8,
Line 28, delete "extending into said base plate and opening onto said" and replace with -- extending into said base plate and opening onto said socket interior; --.

Signed and Sealed this

Twenty-eighth Day of February, 2006

JON W. DUDAS
*Director of the United States Patent and Trademark Office*